United States Patent
Tegg et al.

(10) Patent No.: US 12,121,290 B2
(45) Date of Patent: Oct. 22, 2024

(54) ELECTRODE ASSEMBLY INCLUDING EXPANDABLE ISOLATION MEMBER

(71) Applicant: St. Jude Medical, Cardiology Division, Inc., St. Paul, MN (US)

(72) Inventors: Troy Tegg, Elk River, MN (US); Salo Arias, Brooklyn Park, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 227 days.

(21) Appl. No.: 17/247,770

(22) Filed: Dec. 22, 2020

(65) Prior Publication Data

US 2021/0267672 A1  Sep. 2, 2021

Related U.S. Application Data

(60) Provisional application No. 62/983,200, filed on Feb. 28, 2020.

(51) Int. Cl.
*A61B 18/14* (2006.01)
*A61B 18/00* (2006.01)

(52) U.S. Cl.
CPC .. *A61B 18/1492* (2013.01); *A61B 2018/0022* (2013.01); *A61B 2018/00577* (2013.01); *A61B 2018/00613* (2013.01)

(58) Field of Classification Search
CPC ........ A61B 18/1492; A61B 2018/0022; A61B 2018/00577; A61B 2018/00613
See application file for complete search history.

(56) References Cited

U.S. PATENT DOCUMENTS 5,540,679 A * 7/1996 Fram ................... A61B 18/082
607/101
9,724,170 B2 * 8/2017 Mickelsen ........ A61M 25/0606
(Continued)

FOREIGN PATENT DOCUMENTS

CN        1269708 A    10/2000
CN      102686180 A     9/2012
(Continued)

OTHER PUBLICATIONS

EESR for European patent application No. 23197863.6, Nov. 12, 2023, 8 pages.
(Continued)

*Primary Examiner* — Ronald Hupczey, Jr.
*Assistant Examiner* — Abigail Bock
(74) *Attorney, Agent, or Firm* — Armstrong Teasdale LLP

(57) ABSTRACT

An electrode assembly includes an electrode pair including a first electrode and a second electrode configured to be selectively energized for delivery of electroporation therapy. The electrode assembly also includes an expandable isolation member disposed axially between the first electrode and the second electrode. One of the first electrode and the second electrode is positioned proximally of a proximal end of the expandable isolation member and the other of the first electrode and the second electrode is positioned distal to a distal end of the expandable isolation member. The expandable isolation member is configurable between a collapsed configuration and an expanded configuration. The expandable isolation member includes a circumferential sealing surface configured for sealing engagement with tissue of a patient such that the expandable isolation member inhibits fluid and electrical communication between the first electrode and the second electrode when engaged with the tissue.

19 Claims, 7 Drawing Sheets

(56) References Cited

U.S. PATENT DOCUMENTS

| | | | |
|---|---|---|---|
| 10,660,702 B2 * | 5/2020 | Viswanathan | A61B 18/1492 |
| 2005/0288730 A1 | 12/2005 | Deem et al. | |
| 2008/0172050 A1 | 7/2008 | Satake | |
| 2012/0232326 A1 | 9/2012 | Habib | |
| 2015/0182740 A1 | 7/2015 | Mickelsen | |
| 2017/0065339 A1 * | 3/2017 | Mickelsen | A61B 18/1492 |
| 2018/0140807 A1 | 5/2018 | Herrera et al. | |
| 2018/0228534 A1 | 8/2018 | Govari et al. | |
| 2019/0231421 A1 | 8/2019 | Viswanathan | |
| 2019/0343580 A1 | 11/2019 | Nguyen et al. | |
| 2020/0398048 A1 * | 12/2020 | Krimsky | A61N 1/205 |

FOREIGN PATENT DOCUMENTS

| | | |
|---|---|---|
| CN | 104546117 A | 4/2015 |
| CN | 107456273 A | 12/2017 |
| CN | 108096685 A | 6/2018 |
| CN | 108523989 A | 9/2018 |
| CN | 110267615 A | 9/2019 |
| JP | 2002510229 A | 4/2002 |
| JP | 2008167958 A | 7/2008 |
| JP | 2009528911 A | 8/2009 |
| JP | 2014502195 A | 1/2014 |
| JP | 2016532497 A | 10/2016 |
| WO | 2015019784 A1 | 4/2015 |
| WO | 2015171921 A2 | 11/2015 |
| WO | 2018106538 A1 | 6/2018 |
| WO | 2019084442 A1 | 5/2019 |
| WO | 2019133608 A1 | 7/2019 |
| WO | 2021113463 A1 | 6/2021 |

OTHER PUBLICATIONS

International Search Report and Written Opinion for International Patent Application No. PCT/US2020/066647, mailed Mar. 25, 2021, 14 pages.

* cited by examiner

ELECTRODE ASSEMBLY INCLUDING EXPANDABLE ISOLATION MEMBER

CROSS-REFERENCE TO RELATED APPLICATIONS

This application claims priority to U.S. Provisional Patent Application Ser. No. 62/983,200, filed Feb. 28, 2020, the disclosure of which is hereby incorporated by reference in its entirety.

BACKGROUND OF THE DISCLOSURE a. Field of the Disclosure

The present disclosure relates generally to medical devices that are used in the human body. In particular, the present disclosure relates to electroporation systems and electrode assemblies having an expandable isolation member that are usable in such electroporation systems.

b. Background

Various therapies are used to treat various conditions afflicting the human anatomy. Cardiac arrhythmias, for example are sometimes treated using ablation therapy. When tissue is ablated, or at least subjected to ablative energy generated by an ablation generator and delivered by an ablation catheter, lesions form in the tissue. Electrodes mounted on or in ablation catheters are used to create tissue necrosis in cardiac tissue to correct conditions such as atrial arrhythmia (including, but not limited to, ectopic atrial tachycardia, atrial fibrillation, and atrial flutter). Arrhythmia (i.e., irregular heart rhythm) can create a variety of dangerous conditions including loss of synchronous atrioventricular contractions and stasis of blood flow that can lead to a variety of ailments and even death. It is believed that the primary cause of atrial arrhythmia is stray electrical signals within the left or right atrium of the heart. The ablation catheter imparts ablative energy (e.g., radiofrequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

One candidate for use in therapy of cardiac arrhythmias is electroporation. Electroporation therapy involves electric field-induced pore formation on the cell membrane. The electric field may be induced by applying a direct current (DC) signal delivered as a relatively short-duration pulse. Such a pulse may be repeated to form a pulse train. When such an electric field is applied to tissue in vivo, the cells in the tissue are subjected to trans-membrane potential, which opens the pores on the cell wall, hence the term electroporation. Electroporation may be reversible (i.e., the temporally-opened pores will reseal) or irreversible (i.e., the pores will remain open). For example, in the field of gene therapy, reversible electroporation (i.e., temporarily open pores) is used to transfect high molecular weight therapeutic vectors into the cells. In other therapeutic applications, a suitably configured pulse train alone may be used to cause cell destruction, for instance by causing irreversible electroporation (IRE).

SUMMARY OF THE DISCLOSURE

The present disclosure is directed to an electroporation system including a catheter shaft, and an electrode assembly coupled to the catheter shaft. The electrode assembly includes an electrode pair including a first electrode and a second electrode configured to be selectively energized for delivery of electroporation therapy. The electrode assembly also includes an expandable isolation member disposed axially between the first electrode and the second electrode. One of the first electrode and the second electrode is positioned proximally of a proximal end of the expandable isolation member and the other of the first electrode and the second electrode is positioned distal to a distal end of the expandable isolation member. The expandable isolation member is configurable between a collapsed configuration and an expanded configuration. The expandable isolation member includes a circumferential sealing surface configured for sealing engagement with tissue of a patient such that the expandable isolation member inhibits fluid and electrical communication between the first electrode and the second electrode when engaged with tissue of the patient. The electroporation system also includes an electroporation generator coupled in communication with the first electrode and the second electrode and configured to supply an electroporation signal thereto for the delivery of the electroporation therapy to the tissue of the patient.

The present disclosure is also directed to an electrode assembly for a catheter system. The electrode assembly includes an electrode pair including an first electrode and a second electrode configured to be selectively energized for delivery of electroporation therapy. The electrode assembly also includes an expandable isolation member disposed axially between the first electrode and the cathode. One of the first electrode and the second electrode is positioned proximally of a proximal end of the expandable isolation member and the other of the first electrode and the second electrode is positioned distal to a distal end of the expandable isolation member. The expandable isolation member is configurable between a collapsed configuration and an expanded configuration. The expandable isolation member includes circumferential sealing surface configured for sealing engagement with tissue of a patient such that the expandable isolation member inhibits fluid and electrical communication between the first electrode and the second electrode when engaged with the tissue of the patient.

The present disclosure is further directed to a method including advancing an electrode assembly to a target tissue site. The electrode assembly extends includes an electrode pair including a first electrode and a second electrode. The electrode assembly also includes an expandable isolation member disposed axially between the first electrode and the second electrode. One of the first electrode and the second electrode is positioned proximally of a proximal end of the expandable isolation member and the other of the first electrode and the second electrode is positioned distal to a distal end of the expandable isolation member. The expandable isolation member is configurable between a collapsed configuration and an expanded configuration, and includes a circumferential sealing surface configured for sealing engagement with tissue of a patient such that the expandable isolation member inhibits fluid and electrical communication between the first electrode and the second electrode when engaged with tissue of the patient. The method also includes transitioning the expandable isolation member from the collapsed configuration to the expanded configuration, engaging the target tissue site with the expandable isolation member to inhibit fluid communication between the first electrode and the second electrode, and supplying an electroporation signal to the first electrode and the second electrode.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

The present disclosure relates generally to medical devices that are used in the human body. In particular, in many embodiments, the present disclosure relates to electroporation systems and electrode assemblies for use in such electroporation systems. The disclosed embodiments may lead to more consistent and improved patient outcomes in electroporation therapy procedures. For example, embodiments of the present disclosure utilize an electrode assembly including an expandable isolation member and a pair of electrodes disposed on opposing ends of the electrode assembly. The expandable isolation member is configured to isolate one electrode from the other (e.g., fluidly and electrically) at a target electroporation location, causing the electric field and corresponding electroporation current to go around the isolation member and through the tissue at the target location. The electrode assembly of the present disclosure facilitates improved localization of electroporation therapy, thereby reducing the required voltage output to induce electroporation in tissue at a target location. Additional embodiments of the present disclosure utilize varying distal electrode assemblies to enable various functions, including point ablation and cardiac tissue mapping.

Although an exemplary embodiment of the present disclosure is described with respect to pulmonary vein isolation (PVI), it is contemplated that the described features and methods of the present disclosure as described herein may be incorporated into any number of systems and any number of applications as would be appreciated by one of ordinary skill in the art based on the disclosure herein.

Figure 1:
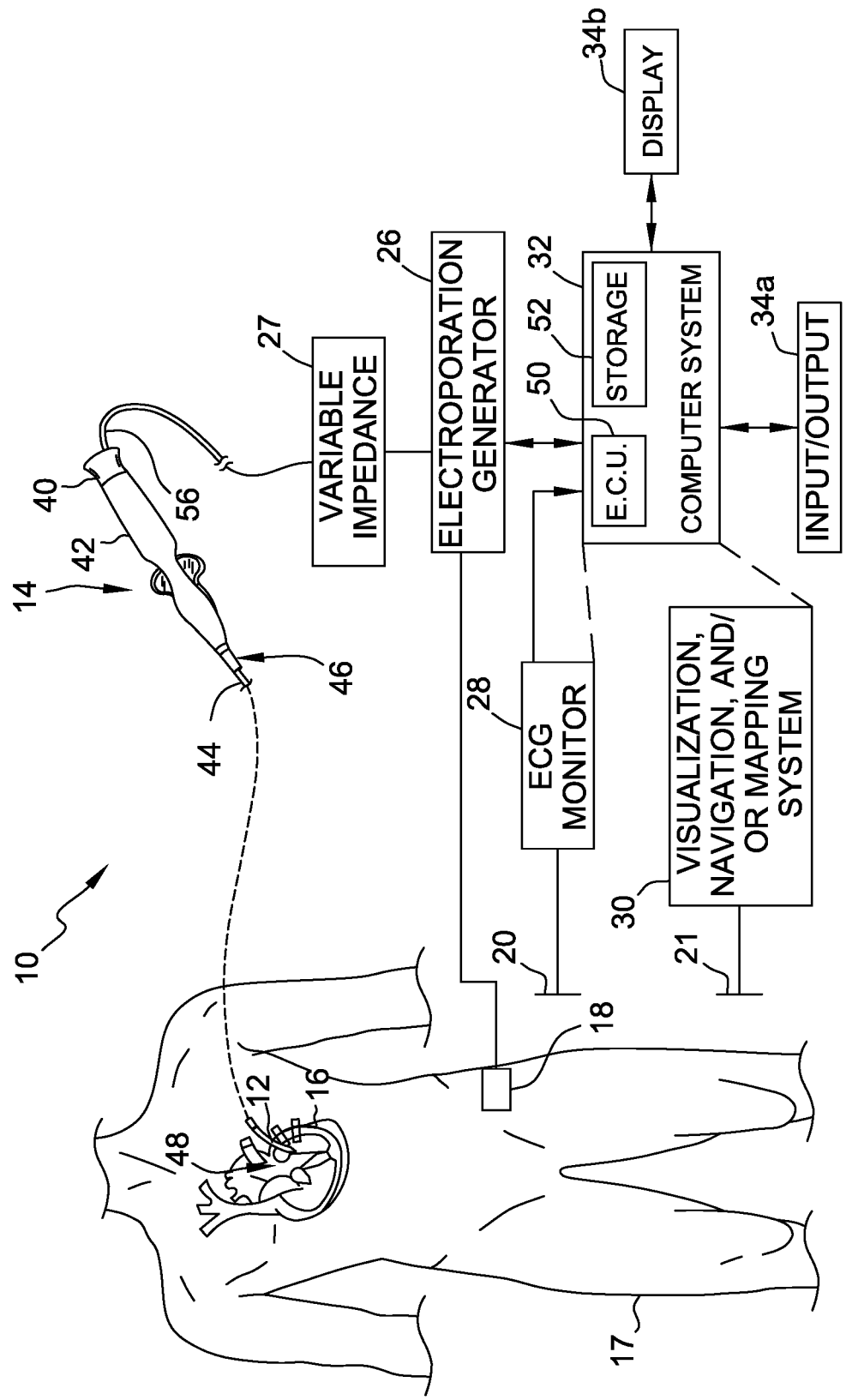
FIG. 1 is a schematic and block diagram view of a system for electroporation therapy.

Referring now to the drawings, FIG. 1 illustrates an exemplary embodiment of a system 10 for electroporation therapy. In general, the various embodiments include an electrode assembly disposed at the distal end of a catheter. As used herein, "proximal" refers to a direction toward the end of the catheter near the clinician and "distal" refers to a direction away from the clinician and (generally) inside the body of a patient. The electrode assembly includes one or more individual, electrically isolated electrode elements. In some embodiments, each electrode element, also referred to herein as a catheter electrode, is individually wired such that it can be selectively paired or combined with any other electrode element to act as a bipolar or a multi-polar electrode.

System 10 may be used for irreversible electroporation (IRE) to destroy tissue. In particular, system 10 may be used for electroporation-induced primary necrosis therapy, which refers to the effects of delivering electrical current in such manner as to directly cause an irreversible loss of plasma membrane (cell wall) integrity leading to its breakdown and cell necrosis. This mechanism of cell death may be viewed as an "outside-in" process, meaning that the disruption of the outside wall of the cell causes detrimental effects to the inside of the cell. Typically, for plasma membrane electroporation, electric current is delivered as a pulsed electric field in the form of short-duration direct current (DC) pulses between closely spaced electrodes capable of delivering an electric field strength sufficient to cause irreversible electroporation in the targeted cells. In some particular embodiments, system 10 is configured to deliver an electroporation pulse signal having a relatively high voltage and low pulse duration.

Irreversible electroporation through a multielectrode catheter, as described further herein, may enable pulmonary vein isolation in as few as one shock per vein, which may produce much shorter procedure times compared to sequentially positioning a radiofrequency (RF) ablation catheter tip around a vein. It should be understood that the mechanism of cell destruction in electroporation is not primarily due to heating effects, but rather due to cell membrane disruption through application of a high-voltage electric field. Thus, electroporation may avoid some possible thermal effects that may occur when using RF energy. This "cold" or "non-thermal" therapy thus has desirable characteristics.

It should be understood that while energization strategies may be described as involving DC pulses, embodiments may use variations of DC pulses. For example, exponentially-decaying pulses, exponentially-increasing pulses, and combinations thereof may be used. In yet other embodiments, energization strategies involving alternating current (AC) pulses may be used for IRE therapy.

System 10 includes a catheter electrode assembly 12 including at least one catheter electrode configured to be used as briefly outlined above and as described in greater detail below. Electrode assembly 12 is incorporated as part of a medical device such as a catheter 14 for electroporation therapy of tissue 16 in a body 17 of a patient. In the illustrative embodiment, tissue 16 comprises heart or cardiac tissue. It should be understood, however, that embodiments may be used to conduct electroporation therapy with respect to a variety of other body tissues.

FIG. 1 further shows a plurality of return electrodes designated 18, 20, and 21 that are diagrammatic of the body connections that may be used by the various sub-systems included in the overall system 10, such as an electroporation generator 26, an electrophysiology (EP) monitor such as an ECG monitor 28, a visualization, navigation, and/or mapping system 30 for visualization, mapping and navigation of internal body structures. In the illustrated embodiment, return electrodes 18, 20, and 21 are patch electrodes. It should be understood that the illustration of a single patch electrode is diagrammatic only (for clarity), and that such sub-systems to which these patch electrodes are connected may, and typically will, include more than one patch (body surface) electrode. In other embodiments, return electrodes 18, 20, and 21 may be any other type of electrode suitable for use as a return electrode including, for example, one or more catheter electrodes. Return electrodes that are catheter electrodes may be part of electrode assembly 12 or part of a separate catheter (not shown). In some embodiments, for example, system 10 includes a bipolar catheter electrode assembly 12 that includes at least one electrode pair including two electrodes, with one electrode functioning as the return electrode.

Electroporation generator 26 is configured to energize the electrode element(s) of electrode assembly 12 in accordance with an electroporation energization strategy, which may be predetermined or may be user-selectable. For electroporation-induced primary necrosis therapy, generator 26 may be configured to produce an electric current that is delivered via electrode assembly 12 as a pulsed electric field in the form of short-duration DC pulses transmitted between the pair of electrodes of electrode assembly 12 and capable of delivering an electric field strength of about 0.1 to 1.0 kV/cm (e.g., at the tissue site). The voltage amplitude and pulse duration needed for irreversible electroporation are inversely related. For example, as pulse durations are decreased, the voltage amplitude must be increased to achieve electroporation.

In some embodiments, electroporation generator 26, sometimes also referred to herein as a DC energy source, is a biphasic electroporation generator 26 configured to generate a series of DC pulses with alternating polarities—i.e., consecutive DC pulses that produce current in alternating directions. In other embodiments, electroporation generator is a monophasic or polyphasic electroporation generator. In some embodiments, electroporation generator 26 is configured to output energy in DC pulses at selectable energy levels, such as fifty joules, one-hundred joules, two-hundred joules, and the like. Other embodiments may have more or fewer energy settings, and the values of the available settings may be the same or different. In some embodiments, electroporation generator 26 outputs or generates a DC pulse having a peak magnitude of between about 500 V and about 3.5 kV, between about 500 V and 2.5 kV, between about 600 V and 3.0 kV, between about 800 V and about 3.5 kV, between about 600 V and about 2.5 kV, between about 800 V and about 2.5 kV, between about 1.0 kV and about 3.5 kV, between about 600 V and about 1.5 kV, between about 800 V and about 2.0 kV, or between about 1.0 kV and about 2.5 kV. Other embodiments may output or generate any other suitable voltage.

In some embodiments, electroporation generator 26 outputs or generates a DC pulse having a pulse duration in the range of 1 nanosecond to 100 microseconds (µs), 1 nanosecond to 50 µs, 0.1 µs to 100 µs, 1 nanosecond to 20 µs, 0.1 µs to 50 µs, 1 µs to 100 µs, 1 nanosecond to 15 µs, 0.1 µs to 20 µs, 0.5 µs to 50 µs, 1 nanosecond to 10 µs, 0.1 µs to 15 µs, 1 nanosecond to 5 µs, 0.1 µs to 10 µs, 0.1 µs to 5 µs, less than 5 µs, less than 4 µs, less than 3 µs, and less than 2 µs. In other embodiments, pulse signals generated by electroporation generator 26 can have a voltage amplitude less than 500 V or greater than 3.5 kV, and can have a pulse duration greater than 100 µs or less than 1 nanosecond.

In one example, electroporation generator 26 outputs or generates a biphasic pulse signal having a voltage amplitude in the range of 500 V to 3.5 kV, in the range of 500 V to 2.5 kV, in the range of 600 V to 3.0 kV, in the range of 600 V to 2.5 kV, or in the range of 800 V to 2.5 kV, and each phase of the biphasic pulse signal has a pulse duration in the range of 400 nanoseconds to 20 µs, or in the range of 500 nanoseconds to 1.5 µs. Additionally, phases of the biphasic pulse signal can be offset by a non-zero interval, for example, in the range of 350 nanoseconds to 1 ms, or in the range of 500 nanoseconds to 1.5 µs.

Additional description of electroporation generator 26 and DC pulse characteristics suitable for use with the electrode assemblies described herein are disclosed in U.S. patent application Ser. No. 17/247,198, filed Dec. 3, 2020, the disclosure of which is hereby incorporated by reference in its entirety. In yet other embodiments, electroporation generator 26 configured to generate pulses involving an AC signal.

A variable impedance 27 allows the impedance of the system to be varied. Moreover, variable impedance 27 may be used to change one or more characteristics, such as amplitude, duration, pulse shape, and the like, of an output of electroporation generator 26. Although illustrated as a separate component, variable impedance 27 may be incorporated in catheter 14 or generator 26. Variable impedance 27 includes one or more impedance elements, such as resistors, capacitors, or inductors (not shown) connected in series, parallel, or combinations of series and/or parallel. In the illustrated embodiment, variable impedance 27 is connected in series with catheter 14. Alternatively, the impedance elements of variable impedance 27 may be connected in parallel with catheter 14 or in a combination of series and parallel with catheter 14. Moreover, in other embodiments, the impedance elements of variable impedance 27 are connected in series and/or parallel with return electrode 18. Some embodiments include more than one variable impedance 27, each of which may include one or more impedance elements. In such embodiments, each variable impedance 27 may be connected to a different catheter electrode or group of catheter electrodes to allow the impedance through each catheter electrode or group of catheter electrodes to be independently varied. In other embodiments, the impedance of system 10 may not need to be varied and variable impedance 27 may be omitted.

System 10 may further include a main computer system 32 (including an electronic control unit 50 and data storage or memory 52), which may be integrated with system 30 in certain embodiments. System 32 may further include conventional interface components, such as various user input/output mechanisms 34a and a display 34b, among other components.

In the illustrative embodiment, catheter 14 includes a cable connector 40, or interface, a handle 42, and a shaft 44 having a proximal end 46 and a distal end 48. Catheter 14 may also include other conventional components not illustrated herein such as a temperature sensor, additional electrodes, and corresponding conductors or leads. Connector 40 provides mechanical and electrical connection(s) for a cable 56 extending from generator 26. Connector 40 may include conventional components known in the art and, as shown, is disposed at the proximal end of catheter 14.

Handle 42 provides a location for the clinician to hold catheter 14 and may further provide means for steering or guiding shaft 44 within body 17. For example, handle 42 may include means to change the length of a guidewire extending through catheter 14 to distal end 48 of shaft 44 or means to steer shaft 44. Moreover, in some embodiments, handle 42 may be configured to vary the shape, size, and/or orientation of a portion of the catheter and/or electrode assembly 12. Handle 42 is also conventional in the art and it will be understood that the construction of handle 42 may vary. In an alternate exemplary embodiment, catheter 14 may be robotically driven or controlled. Accordingly, rather than a clinician manipulating a handle to advance/retract and/or steer or guide catheter 14 (and shaft 44 thereof in particular), a robot is used to manipulate catheter 14.

Shaft 44 is an elongated, tubular, flexible member configured for movement within body 17. Shaft 44 is configured to support electrode assembly 12 as well as contain associated conductors, and possibly additional electronics used for signal processing or conditioning. Shaft 44 may also permit transport, delivery and/or removal of fluids (including irrigation fluids, bodily fluids, and inflation fluids), medicines, and/or surgical tools or instruments. Shaft 44 may be made from conventional materials such as polyurethane and defines one or more lumens configured to house and/or transport electrical conductors, fluids, or surgical tools. Shaft 44 may be introduced into a blood vessel or other structure within body 17 through a conventional introducer. Shaft 44 may then be advanced, retracted, and/or steered or guided through body 17 to a desired location such as the site of tissue 16, including through the use of guidewires or other means known in the art.

Figure 2:
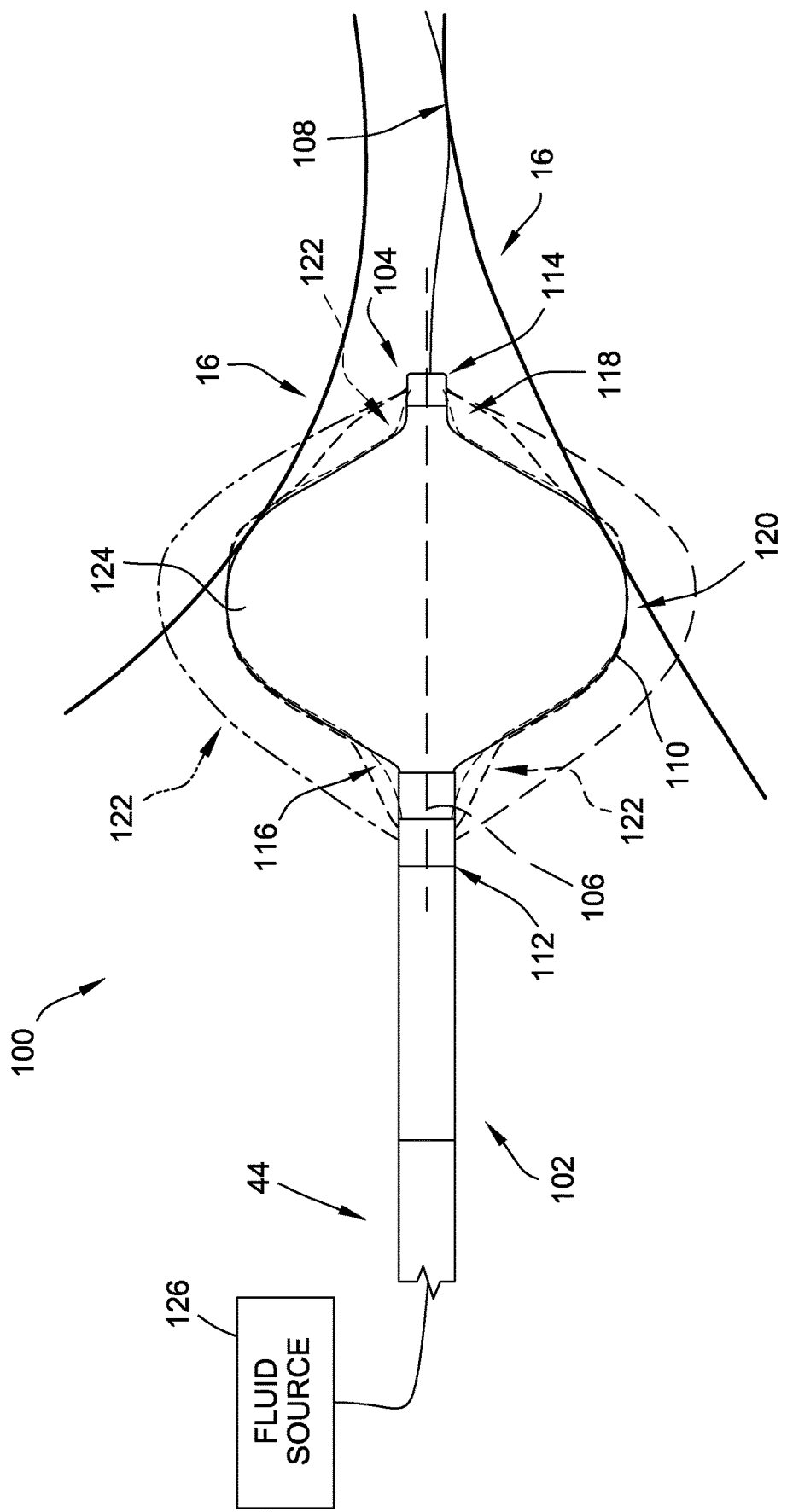
FIG. 2 is a side view of a first exemplary electrode assembly suitable for use in the system of FIG. 1.

FIG. 2 illustrates an exemplary electrode assembly 12 suitable for use in system 10, illustrated in the form of an expandable electrode assembly 100. Electrode assembly 100 extends axially from a proximal end 102 of electrode assembly 100 to a distal end 104 of electrode assembly 100, generally along a longitudinal axis 106. Proximal end 102 is coupled to catheter shaft 44 (e.g., to a distal end of shaft 44) via a suitable coupler (not shown). In the exemplary embodiment, a guidewire 108 extends axially through shaft 44 and through electrode assembly 100. Guidewire 108 may be manipulated (e.g., using handle 42) to adjust a position of electrode assembly 100 within body 17.

Electrode assembly 100 generally includes an expandable isolation member 110 and a pair of electrodes 112, 114. More specifically, expandable isolation member 110 extends between a proximal end 116 of expandable isolation member 110 and a distal end 118 of expandable isolation member 110. Electrodes 112, 114 are arranged adjacent proximal end 116 and distal end 118 of expandable isolation member 110, respectively, such that expandable isolation member 110 is disposed axially between electrodes 112, 114. A proximal electrode 112 is positioned adjacent proximal end 116 of expandable isolation member 110 and is positioned proximate to proximal end 102 of electrode assembly 100. Likewise, a distal electrode 114 is positioned adjacent to distal end 118 of expandable isolation member 110 and is proximate to distal end 104 of electrode assembly 100. Distal end 118 of expandable isolation member 110 is proximal to distal end 104 of electrode assembly 100 in the exemplary embodiment.

Electrodes 112, 114 may be used for a variety of diagnostic and therapeutic purposes including, for example and without limitation, cardiac mapping and/or ablation (e.g., IRE ablation). For example, electrode assembly 100 may be configured as a bipolar electrode assembly for use in bipolar-based electroporation therapy. Specifically, as described above, electrodes 112, 114 are individually electrically coupled to generator 26 (e.g., via suitable electrical wire or other suitable electrical conductors extending through catheter shaft 44) and are configured to be selectively energized (e.g., by electroporation generator 26 and/or computer system 32) with opposite polarities to generate a potential and corresponding electric field therebetween, for IRE therapy. That is, one of electrodes 112, 114 is configured to function as a cathode, and the other is configured to function as an anode. For example, in a first embodiment, electrode 112 is an anode and electrode 114 is a cathode. In a second embodiment, electrode 112 is a cathode and electrode 114 is an anode. Electrodes 112, 114 may be any suitable electroporation electrodes. In the exemplary embodiment, electrodes 112, 114 are ring electrodes. Electrodes 112, 114 may have any other shape or configuration. It is realized that the shape, size, and/or configuration of electrodes 112, 114 may impact various parameters of the applied electroporation therapy. For example, increasing the surface area of one or both electrodes 112, 114 may reduce the applied voltage needed to cause the same level of tissue destruction. Moreover, although each of proximal electrode 112 and distal electrode 114 are illustrated as single electrodes, either or both of proximal electrode 112 and distal electrode 114 may be alternatively embodied as two or more discrete electrodes. Further, while electrode assembly 100 is described as a bipolar electrode assembly, it should be understood that in some embodiments, electrode assembly 100 may be configured as a monopolar electrode assembly and use a patch electrode (e.g., return electrode 18) as a return or indifferent electrode.

In the exemplary embodiment, expandable isolation member 110 is configurable between a collapsed configuration (not shown) and an expanded configuration (as shown in FIG. 2). For example, expandable isolation member 110 is delivered in the collapsed configuration to the target location of tissue 16 within body 17 (e.g., axially disposed within catheter shaft 44) and transitioned to the expanded configuration at the target location. Expandable isolation member 110 is configured to sealingly engage with tissue 16 at the target location and to inhibit electrical communication between electrodes 112, 114 (e.g., by at least partially insulating distal electrode 114 from proximal electrode 112). More specifically, expandable isolation member 110, as described further herein, is formed from an electrically insulating material. Therefore, a current flow 122 between proximal electrode 112 and distal electrode 114 is diverted around expandable isolation member 110. FIG. 2 depicts a plurality of current flows 122 of varying shape and magnitude of diversion around expandable isolation member 110. In some embodiments, the shape and size of expandable isolation member 110 may be selected to influence current flow 122 therearound (e.g., a magnitude of diversion, a shape or direction of the resulting current flow 122, etc.).

Moreover, expandable isolation member 110 is configured to sealingly engage tissue 16 when in the expanded configuration. In one exemplary embodiment, expandable isolation member 110 includes a circumferential sealing surface 120 configured for sealing engagement with tissue 16 such that expandable isolation member 110 inhibits fluid communication and, consequently, electrical communication (e.g., current flow), between the electrodes 112, 114 when engaged with tissue of the patient. For example, where expandable isolation member 110 is used for PVI or to isolate other cylindrical or tubular tissue (e.g., other vasculature tissue), expandable isolation member 110 may occlude the pulmonary vein and inhibit or substantially prevent the flow of blood therearound. Therefore, when electrodes 112, 114 are energized, current 122 flows therebetween through tissue 16 adjacent expandable isolation member 110, rather than through blood. In this way, the electroporation therapy may be more localized and, therefore, require reduced applied voltage to cause the desired amount of cell destruction. Specifically, fluid (e.g., blood) is more electrically conductive than tissue, therefore current flows through blood more readily than through tissue, and electroporation therapy is less effective. By blocking the blood flow as described herein, the current 122 between electrodes 112, 114 is diverted through adjacent tissue 16, thereby increasing the effectiveness of electroporation therapy at a given voltage.

In the exemplary embodiment, expandable isolation member 110 includes an outer layer 124 formed or constructed from an electrically insulating material. For example, outer layer 124 may include polyethylene terephthalate (PET). Outer layer 124 may include any other suitable material that is electrically insulating and able to accommodate expansion and contraction of electrode assembly 100. In certain embodiments, as shown in FIG. 2, expandable isolation member 110 is embodied as an inflatable balloon. In such embodiments, the inflatable balloon is coupled to a fluid source 126 for selectively inflating the balloon (e.g., when electrode assembly 100 has been advanced to the target location within body 17 and has been deployed from catheter shaft 44). In some embodiments, the fluid source includes a dielectric fluid, such as deionized water, saline, carbon dioxide gas, nitrous oxide gas, and/or air. In other embodiments, expandable isolation member 110 may be selectively expanded using other means, such as an expandable frame (e.g., a frame formed from a shape-memory material) retained within outer layer 124.

Although expandable isolation member 110 is shown in FIG. 2 as having an elongated spherical shape, expandable isolation member 110 may have any other shape or configuration the enables sealing—and, therefore, inhibiting fluid and/or electrical communication between electrodes 112, 114. The particular shape and/or configuration may be selected for the particular tissue isolation desired.

For example, in other embodiments, isolation and tissue destruction within solid or planar tissue, such as the wall of a heart chamber (as opposed to the relatively cylindrical isolation of a vessel), may be desired. In such embodiments, distal end 118 of expandable isolation member 110 may be inverted and concave, and distal electrode 114 is positioned within the concavity of distal end 118. Distal end 118 may be engaged or pressed against the tissue to seal or isolate distal electrode 114 from proximal electrode 112, such that current flow 122 between electrodes 112, 114 is diverted through the tissue (e.g., of the heart chamber wall) engaged with distal end 118.

It is contemplated that full sealing between expandable isolation member 110 and the adjacent tissue 16 may not occur. For example, circumferential sealing surface 120 may not be fully engaged with tissue 16, and some fluid (blood) flow past circumferential sealing surface 120 may occur. In some embodiments, complete engagement or sealing is not necessary for electroporation therapy to proceed successfully. The level of sealing may be ascertained using a variety of methods. In some embodiments, introducing fluoroscopic contrast materials are introduced into the blood stream upstream of expandable isolation member 110, and the presence or amount of contrast material downstream of expandable isolation member 110 is determined using x-rays. In other embodiments, Doppler ultrasound is used to determine the level of fluid flow past expandable isolation member 110. In still other embodiments, impedance between electrodes 112, 114 is measured before and after placement of electrode assembly 100 at the target location; a threshold shift in impedance reflects sufficient sealing. In yet other embodiments, electrode assembly 100 includes a pressure transducer (not shown) on distal end 104 that is used to measure fluid pressure to reflect the level of sealing between expandable isolation member 110 and tissue 16. Additional and/or alternative methods to determine the level of sealing may be used. Moreover, any of the above-described methods can be employed iteratively. Specifically, an initial level of sealing may be determined, and, in response, a position of electrode assembly 100 may be adjusted. A subsequent level of sealing may be determined, and so forth, until an adequate or sufficient level of sealing is reached (e.g., based on threshold values and/or physician determination).

Moreover, based on the determined level of sealing using any of the above methods (or any other suitable method), an appropriate level of voltage to be applied may be selected. A reduced level of sealing may require an increased applied voltage.

Figure 3:
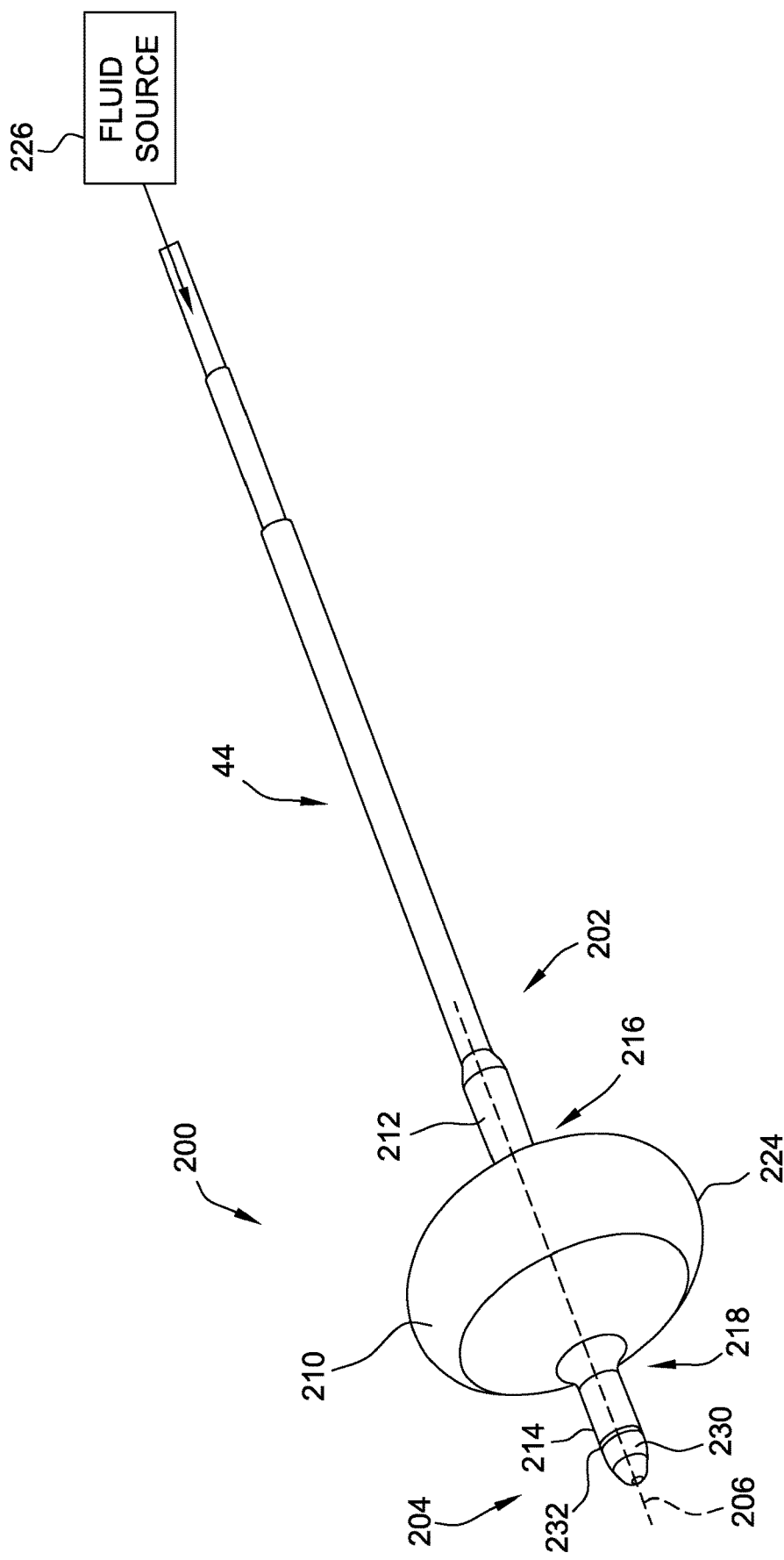
FIG. 3 is a perspective view of another exemplary electrode assembly suitable for use in the system of FIG. 1.
Figure 4:
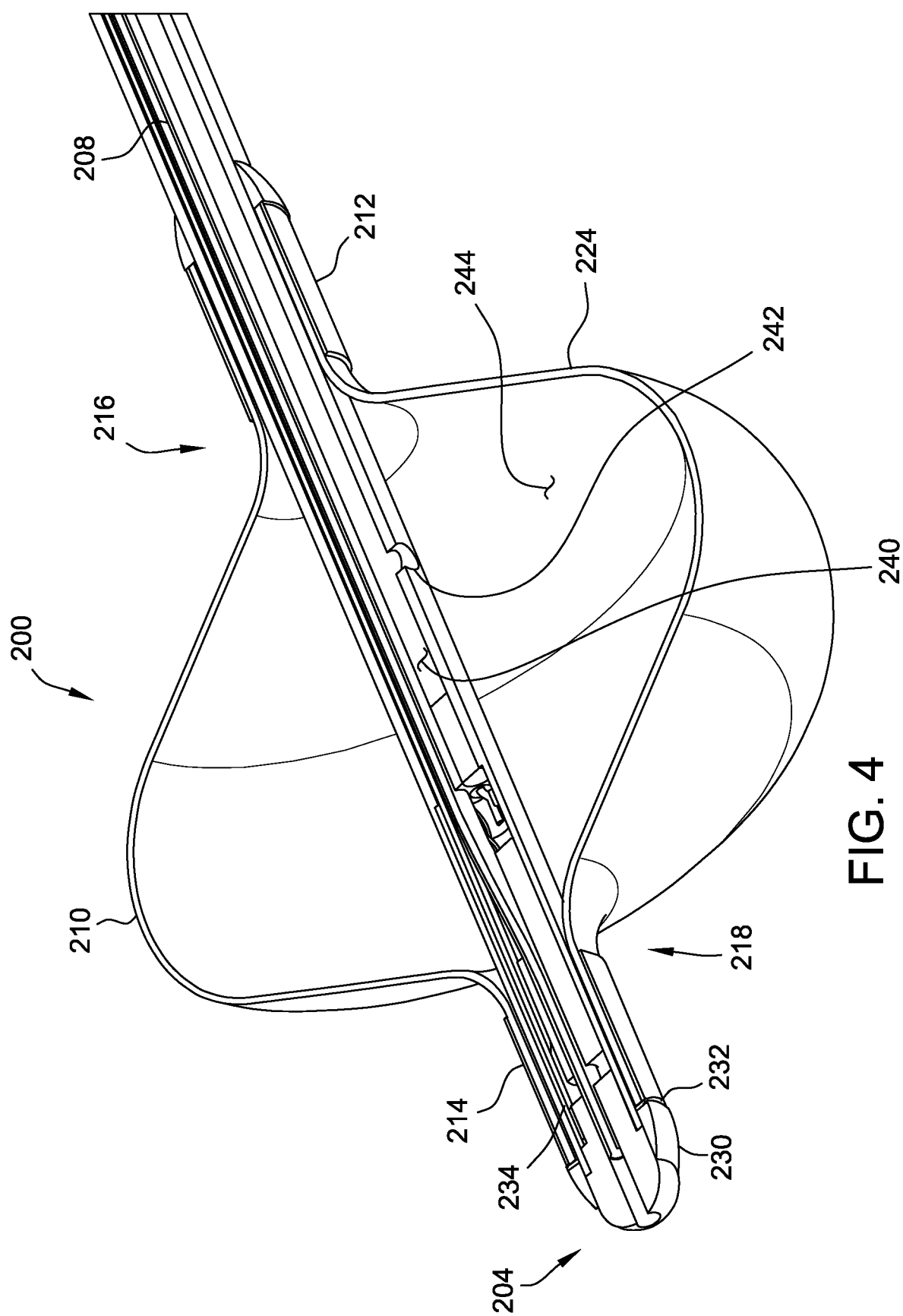
FIG. 4 is a section view of the electrode assembly shown in FIG. 3.

FIGS. 3 and 4 are perspective and sectional views, respectively, of another exemplary electrode assembly 12 suitable for use in system 10, illustrated in the form of an expandable electrode assembly 200. Electrode assembly 200 is similar to electrode assembly 100 in many aspects, with like elements in electrode assembly 200 labeled with a corresponding reference numeral in the 200-range. In particular, electrode assembly 200 extends axially from a proximal end 202 of electrode assembly 200 to a distal end 204 of electrode assembly 200, generally along a longitudinal axis 206. Proximal end 202 is coupled to catheter shaft 44 (e.g., to a distal end of shaft 44) via a suitable coupler (not shown). In the exemplary embodiment, a guidewire 208 (see FIG. 4) extends axially through shaft 44 and through electrode assembly 200. Guidewire 208 may be manipulated (e.g., using handle 42) to adjust a position of electrode assembly 200 within body 17.

Electrode assembly 200 includes an expandable isolation member 210 and electrodes 212 and 214. Additionally, in the exemplary embodiment, electrode assembly 200 includes a distal tip electrode 230. Electrodes 212 and 214 are arranged adjacent to a proximal end 216 and a distal end 218 of expandable isolation member 210, respectively, such that expandable isolation member 210 is disposed axially between electrodes 212, 214. Specifically, a proximal electrode 212 is adjacent proximal end 216 of expandable isolation member 210 and is proximate to proximal end 102 of electrode assembly 200. Likewise, a distal electrode 214 is adjacent distal end 218 of expandable isolation member 210 and is proximate to distal end 204 of electrode assembly 200. Distal end 218 of expandable isolation member 210 is proximal to distal end 204 of electrode assembly 200 in the exemplary embodiment.

Distal tip electrode 230 is positioned distal to distal electrode 214. Distal tip electrode 230 is physically separated and electrically isolated from distal electrode 230 by an electrically insulating member 232 (e.g., an annular interface element formed from an electrically insulative material).

Electrodes 212, 214 may be used for a variety of diagnostic and therapeutic purposes including, for example and without limitation, cardiac mapping and/or ablation (e.g., IRE ablation). For example, electrode assembly 200 may be configured as a bipolar electrode assembly for use in bipolar-based electroporation therapy, as described above with respect to electrode assembly 100. Specifically, as described above, electrodes 212, 214 are configured to be selectively energized (e.g., by electroporation generator 26 and/or computer system 32) with opposite polarities to generate a potential and corresponding electric field therebetween, for IRE therapy. That is, one of electrodes 212, 214 is configured to function as a cathode, and the other is configured to function as an anode.

Distal tip electrode 230 may also be used for a variety of diagnostic and therapeutic purposes including, for example and without limitation, cardiac mapping and/or point ablation (e.g., point IRE ablation). Specifically, distal tip electrode 230 is individually electrically coupled to generator 26 (e.g., via an electrical wire 234 extending through catheter shaft 44). Therefore, each of electrodes 212, 214, and 230 is individually electrically coupled to generator 26 via a separate electrical conductor (e.g., an electrical wire). Distal tip electrode 230 is configured to be selectively energized (e.g., by electroporation generator 26 and/or computer system 32) independently of electrodes 212, 214. In some embodiments, distal tip electrode 230 is energized with an opposite polarity to one of electrodes 212 or 214, to generate a potential and corresponding electric field therebetween, for IRE therapy. In particular, where distal tip electrode 230 is energized with an opposite polarity to distal electrode 214, the electric field generated therebetween may be suitable for point IRE therapy, to precisely target tissue adjacent to distal end 204 of electrode assembly 200. In the exemplary embodiment, distal tip electrode 230 is embodied as a ring electrode. Distal tip electrode 230 may be any suitable electroporation electrode and may have any other shape or configuration.

Further, while electrode assembly 200 is described as a bipolar electrode assembly, it should be understood that in some embodiments, electrode assembly 200 may be configured as a monopolar electrode assembly and use a patch electrode (e.g., return electrode 18) as a return or indifferent electrode. For example, the current path may be directed from distal tip electrode 230 to return electrode 18, in a monopolar therapy application.

In the exemplary embodiment, expandable isolation member 210 is configurable between a collapsed configuration (not shown) and an expanded configuration (as shown in FIGS. 3 and 4). For example, expandable isolation member 210 is delivered in the collapsed configuration to the target location of tissue 16 within body 17 (e.g., axially disposed within catheter shaft 44) and transitioned to the expanded configuration at the target location. As described in greater detail above, expandable isolation member 210 is configured to sealingly engage with tissue 16 at the target location and to inhibit electrical communication between electrodes 212 and 214 and/or between electrodes 230 and 212 (e.g., by at least partially insulating distal electrode 214 and/or distal tip electrode 230 from proximal electrode 212).

In the exemplary embodiment, expandable isolation member 210 includes an outer layer 224 formed or constructed from an electrically insulating material. For example, outer layer 224 may include polyethylene terephthalate (PET) or any other suitable material that is electrically insulating and able to accommodate expansion and contraction of electrode assembly 200. In certain embodiments, as shown in FIGS. 3 and 4, expandable isolation member 210 is embodied as an inflatable balloon. In such embodiments, the inflatable balloon is coupled to a fluid source 226 for selectively inflating the balloon (e.g., when electrode assembly 200 has been advanced to the target location within body 17 and has been deployed from catheter shaft 44). In some embodiments, the fluid source includes a dielectric fluid, such as deionized water, saline, carbon dioxide gas, nitrous oxide gas, and/or air. The inflatable balloon is selectively inflated by channeling the dieletric fluid from fluid source 226, through a fluid lumen 240, and through a fluid port 242 into an internal cavity 244 of the inflatable balloon. In other embodiments, expandable isolation member 210 may be selectively expanded using other means, such as an expandable frame (e.g., a frame formed from a shape-memory material) retained within outer layer 224.

Figure 5:
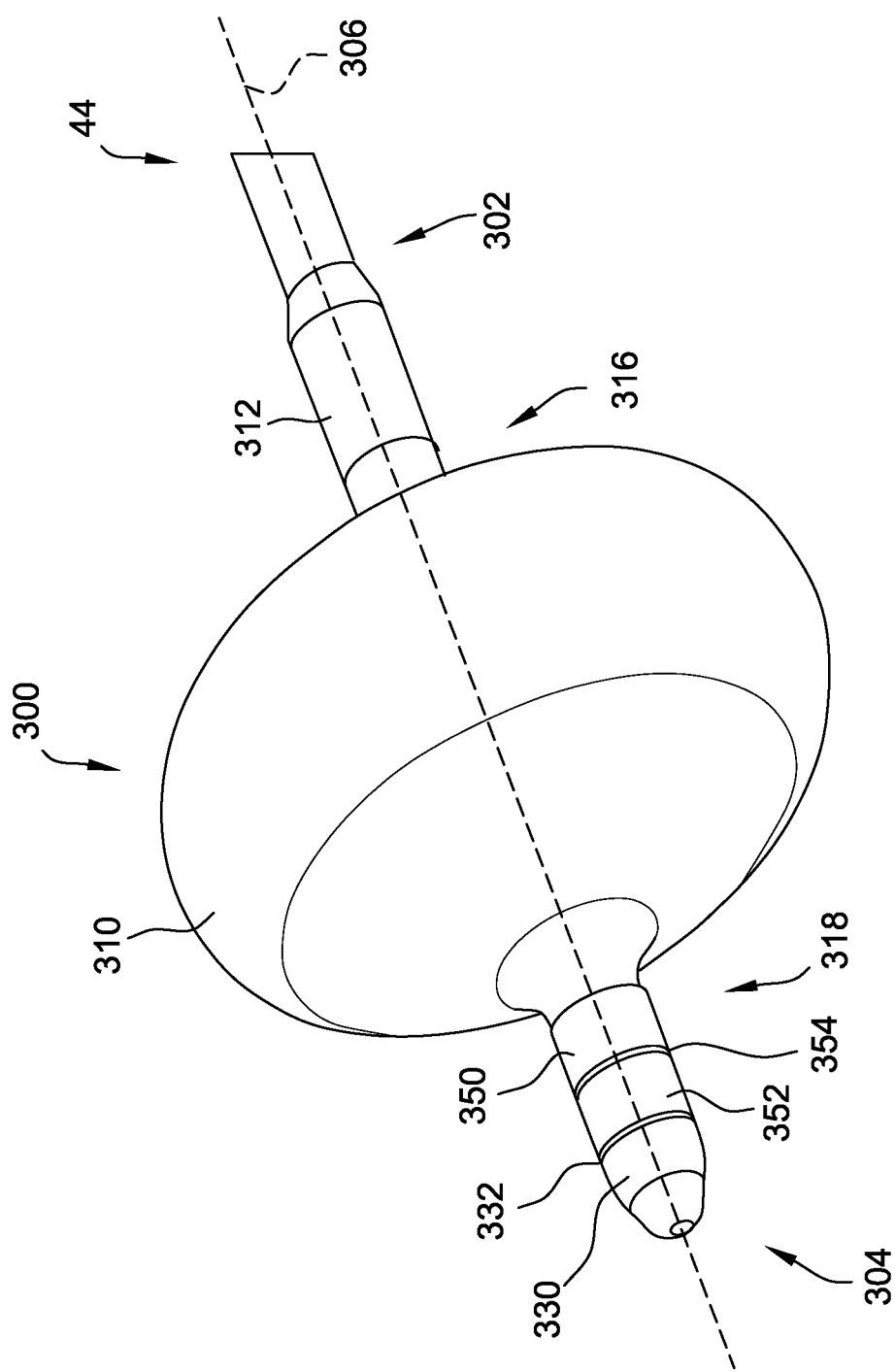
FIG. 5 is a perspective view of another exemplary electrode assembly suitable for use in the system of FIG. 1.

FIG. 5 depicts a perspective view of another exemplary electrode assembly 12 suitable for use in system 10, illustrated in the form of an expandable electrode assembly 300. Electrode assembly 300 is similar to electrode assemblies 100 and 200 in many aspects, with like elements in electrode assembly 300 labeled with a corresponding reference numeral in the 300-range. In particular, electrode assembly 300 extends axially from a proximal end 302 of electrode assembly 300 to a distal end 304 of electrode assembly 300, generally along a longitudinal axis 306. Proximal end 302 is coupled to catheter shaft 44 (e.g., to a distal end of shaft 44) via a suitable coupler (not shown).

Electrode assembly 300 includes an expandable isolation member 310 that extends between a proximal end 316 of expandable isolation member 310 and a distal end 318 of expandable isolation member 310. Electrode assembly 300 also includes a plurality of electrodes, including a proximal electrode 312, a first distal electrode 350, a second distal electrode 352, and a distal tip electrode 330. Proximal electrode 312 is arranged adjacent proximal end 316 of expandable isolation member 310. First distal electrode 350 is arranged adjacent distal end 318 of expandable isolation member 310. Second distal electrode 352 is positioned distal to first distal electrode 350. Second distal electrode 352 is physically separated and electrically isolated from first distal electrode 350 by an electrically insulating member 354. In the exemplary embodiment, the distance between first and second distal electrodes 350, 352 (e.g., a width or depth of insulating member 354) is known, such that first and second distal electrodes 350, 352 are suitable for mapping cardiac tissue. In one embodiment, the distance between first and second distal electrodes 350, 352 (e.g., a width or depth of insulating member 354) is about 0.5 mm.

Distal tip electrode 330 is positioned distal to second distal electrode 352. Distal tip electrode 330 is physically separated and electrically isolated from second distal electrode 352 by an electrically insulating member 332 (e.g., an annular interface element formed from an electrically insulative material).

Electrodes 312, 350, 352, and 330 may be used for a variety of diagnostic and therapeutic purposes including, for example and without limitation, cardiac mapping and/or ablation (e.g., IRE ablation). For example, electrode assembly 300 may be configured as a bipolar electrode assembly for use in bipolar-based electroporation therapy, as described above with respect to electrode assembly 100.

Each electrode 312, 350, 352, and 330 is individually electrically coupled to generator 26 (e.g., via a respective electrical wire or other suitable electrical conductor extending through catheter shaft 44). Each electrode 312, 350, 352, and 330 is configured to be selectively energized (e.g., by electroporation generator 26 and/or computer system 32) independently of one another.

In some embodiments, various pairs or sets of electrodes are energized with an opposite polarity, to generate a potential and corresponding electric field therebetween, for IRE therapy. For example, distal tip electrode 330 may be selectively energized as one of a point cathode or point anode, and second distal electrode 352 or first distal electrode 350 may be selectively energized with an opposite polarity as the other of the point cathode or point anode, for point IRE therapy or point ablation. In another example, distal tip electrode 330 may be selectively energized as one of a cathode or anode, and proximal electrode 312 may be selectively energized with an opposite polarity as the other of the cathode or anode, for IRE therapy of tissue surrounding expandable isolation member 310, as described above with respect to electrode assembly 100. Likewise, either or both of second distal electrode 352 and first distal electrode 350 may be selectively energized as one of a cathode or anode, and proximal electrode 312 may be selectively energized with an opposite polarity as the other of the cathode or anode, for IRE therapy of tissue surrounding expandable isolation member 310, as described above with respect to electrode assembly 100.

In other embodiments, electrode assembly 300 may be configured as a monopolar electrode assembly and use a patch electrode (e.g., return electrode 18) as a return or indifferent electrode. For example, the current path may be directed from distal tip electrode 330 to return electrode 18, in a monopolar therapy application.

Additionally, electrode assembly 300 is suitable for cardiac mapping. For example, bipolar measurements of electrophysiological (EP) data may be made between distal tip electrode 330 and first distal electrode 350, and/or between second distal electrode 352 and first distal electrode 350. Additionally or alternatively, any of electrodes 330, 350, 352 may be used for unipolar mapping (e.g., relative to patch electrode(s) 18, 20, and/or 21).

Figure 6:
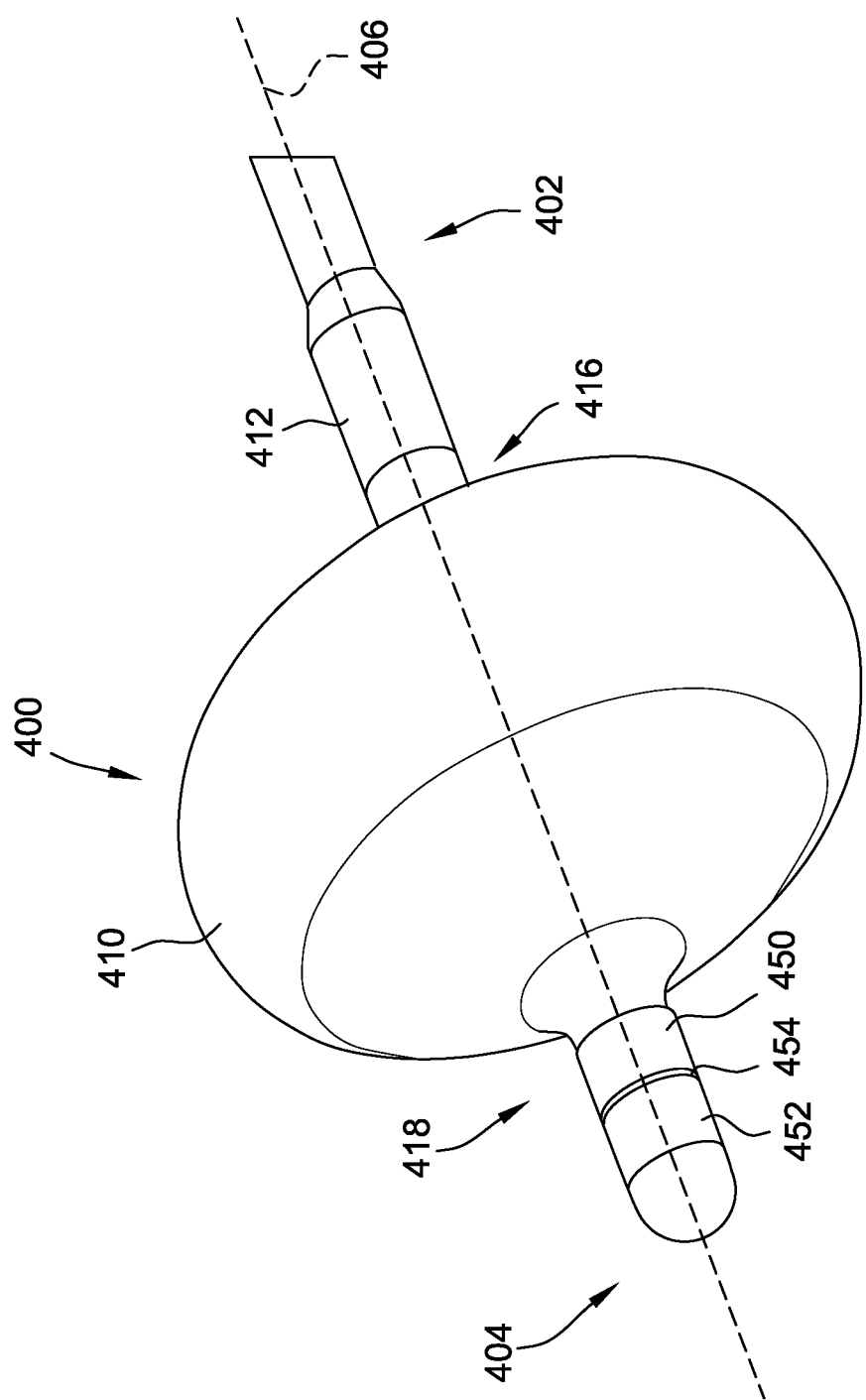
FIG. 6 is a perspective view of another exemplary electrode assembly suitable for use in the system of FIG. 1.

FIG. 6 depicts a perspective view of another exemplary electrode assembly 12 suitable for use in system 10, illustrated in the form of an expandable electrode assembly 400. Electrode assembly 400 is similar to electrode assemblies 100, 200, and 300 in many aspects, with like elements in electrode assembly 400 labeled with a corresponding reference numeral in the 400-range. In particular, electrode assembly 400 is substantially similar to electrode assembly 300, except that electrode assembly 400 does not include a distal tip electrode.

Electrode assembly 400 extends axially from a proximal end 402 to a distal end 404, generally along a longitudinal axis 406. Electrode assembly 400 includes an expandable isolation member 410 that extends between a proximal end 416 of expandable isolation member 310 and a distal end 418 of expandable isolation member 410. Electrode assembly 400 also includes a plurality of electrodes, including a proximal electrode 412, a first distal electrode 450, and a second distal electrode 452. Proximal electrode 412 is arranged adjacent proximal end 416 of expandable isolation member 410. First distal electrode 450 is arranged adjacent distal end 418 of expandable isolation member 410. Second distal electrode 452 is positioned distal to first distal electrode 450. Second distal electrode 452 is physically separated and electrically isolated from first distal electrode 450 by an electrically insulating member 454. In the exemplary embodiment, the distance between first and second distal electrodes 450, 452 (e.g., a width or depth of insulating member 454) is known, such that first and second distal electrodes 450, 452 are suitable for mapping cardiac tissue. In one embodiment, the distance between first and second distal electrodes 450, 452 (e.g., a width or depth of insulating member 454) is about 0.5 mm.

Electrodes 412, 450, and 452 may be used for a variety of diagnostic and therapeutic purposes including, for example and without limitation, cardiac mapping and/or ablation (e.g., IRE ablation). For example, electrode assembly 400 may be configured as a bipolar electrode assembly for use in bipolar-based electroporation therapy, as described above with respect to electrode assembly 100. Each electrode 412, 450, and 452 is individually electrically coupled to generator 26 (e.g., via a respective electrical wire or other suitable electrical conductor extending through catheter shaft 44). Each electrode 412, 450, and 452 is configured to be selectively energized (e.g., by electroporation generator 26 and/or computer system 32) independently of one another. In some embodiments, various pairs or sets of electrodes are energized with an opposite polarity, to generate a potential and corresponding electric field therebetween, for IRE therapy. For example, either or both of second distal electrode 452 and first distal electrode 450 may be selectively energized as one of a cathode or anode, and proximal electrode 412 may be selectively energized with an opposite polarity as the other of the cathode or anode, for IRE therapy of tissue surrounding expandable isolation member 410, as described above with respect to electrode assembly 100. Additionally, electrode assembly 400 is suitable for cardiac mapping. For example, For bipolar measurements of electrophysiological (EP) data may be made between second distal electrode 452 and first distal electrode 450. Additionally or alternatively, first and/or second distal electrode 450, 452 may be used for unipolar mapping (e.g., relative to patch electrode(s) 18, 20, and/or 21).

Figure 7:
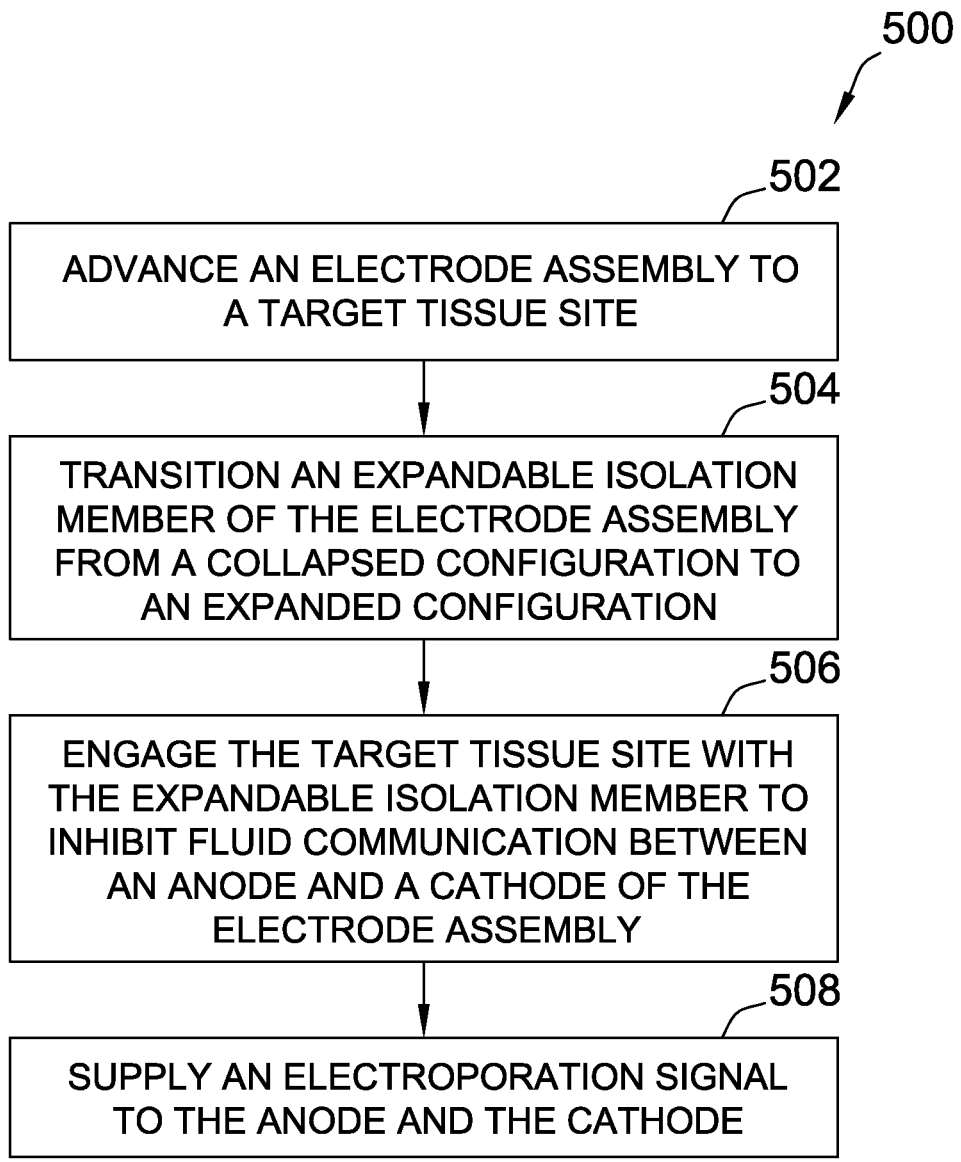
FIG. 7 is a flow diagram of an exemplary method in accordance with the present disclosure.

FIG. 7 is a flow diagram of a method 500 for performing a medical procedure (e.g., electroporation therapy) at a target location using an electrode assembly (e.g., electrode assembly 12, 100, 200, 300, and/or 400, shown in FIGS. 1, 2, 3, 5, and 6, respectively). Method 500 includes advancing 502 the electrode assembly to the target location (e.g., a target tissue site). As described herein, the electrode assembly includes an electrode pair including an anode (e.g., a first electrode) and a cathode (e.g., a second electrode), and an expandable isolation member disposed axially between the anode and the cathode. One of the anode and the cathode is positioned proximally of a proximal end of the expandable isolation member, and the other of the anode and the cathode is positioned distal to a distal end of the expandable isolation member. The expandable isolation member is configurable between a collapsed configuration and an expanded configuration. The expandable isolation member includes a circumferential sealing surface configured for sealing engagement with tissue of a patient such that the expandable isolation member inhibits fluid and electrical communication between the anode and the cathode when engaged with tissue of the patient.

Method 500 also includes transitioning 504 the expandable isolation member from the collapsed configuration to the expanded configuration, and engaging 506 the target tissue site with the expandable isolation member to inhibit fluid communication between the anode and the cathode. Method 500 further includes supplying 508 an electroporation signal to the anode and the cathode.

It should be readily understood that method 500 may include additional, fewer, and/or alternative steps, in other embodiments of the present disclosure. Although certain steps of the example method are numbered, such numbering does not indicate that the steps must be performed in the order listed. Thus, particular steps need not be performed in the exact order they are presented, unless the description thereof specifically require such order. The steps may be performed in the order listed, or in another suitable order.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the invention, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An electroporation system comprising:
a catheter shaft;
an electrode assembly coupled to the catheter shaft, the electrode assembly comprising:
an electrode pair comprising a first electrode and a second electrode configured to be selectively energized for delivery of electroporation therapy; and
an expandable isolation member disposed axially between the first electrode and the second electrode, wherein one of the first electrode and the second electrode is positioned proximally of a proximal end of the expandable isolation member and the other of the first electrode and the second electrode is positioned distal to a distal end of the expandable isolation member, the expandable isolation member configurable between a collapsed configuration and an expanded configuration;
wherein the expandable isolation member comprises a circumferential sealing surface configured for sealing engagement with tissue of a patient such that the expandable isolation member inhibits fluid and electrical communication between the first electrode and the second electrode when engaged with tissue of the patient; and
wherein the one of the first electrode and the second electrode positioned distal to the distal end of the expandable isolation member comprises a pair of ring electrodes separated by an insulating member, wherein the pair of ring electrodes is configured to map the tissue of the patient; and
an electroporation generator coupled in communication with the first electrode and the second electrode and configured to supply an electroporation signal thereto for the delivery of the electroporation therapy to the tissue of the patient, wherein the electroporation system is configured to:
determine a level of sealing between the circumferential sealing surface and the tissue; and
increase a voltage of the electroporation signal to be applied to the tissue based on a reduced level of sealing.

2. The electroporation system of claim 1, wherein the electroporation generator is one of a monophasic electroporation generator, a biphasic electroporation generator, and a polyphasic electroporation generator.

3. The electroporation system of claim 1, wherein the electroporation therapy is irreversible electroporation therapy (IRE).

4. The electroporation system of claim 1, wherein the expandable isolation member comprises an inflatable balloon.

5. The electroporation system of claim 4, wherein the inflatable balloon is coupled to a fluid source for selectively inflating the balloon.

6. The electroporation system of claim 5, wherein the fluid source comprises a dielectric fluid.

7. The electroporation system of claim 6, wherein the fluid source comprises a fluid selected from the group consisting of deionized water, saline, carbon dioxide gas, nitrous oxide gas, and air.

8. The electroporation system of claim 1, wherein the expandable isolation member comprises an outer layer constructed of electrically-insulating material.

9. The electroporation system of claim 1, wherein the first electrode is an anode and the second electrode is a cathode.

10. The electroporation system of claim 1, wherein the electroporation system is further configured to measure an impedance between the first electrode and the second electrode before and after inflation of the expandable isolation member to determine the level of sealing.

11. An electrode assembly for a catheter system configured for delivery of electroporation therapy, the electrode assembly comprising:
an electrode pair comprising a first electrode and a second electrode configured to be selectively energized for delivery of electroporation therapy; and
an expandable isolation member disposed axially between the first electrode and the second electrode, wherein one of the first electrode and the second electrode is positioned proximally of a proximal end of the expandable isolation member and the other of the first electrode and the second electrode is positioned distal to a distal end of the expandable isolation member, the expandable isolation member configurable between a collapsed configuration and an expanded configuration;
wherein the expandable isolation member comprises a circumferential sealing surface configured for sealing engagement with tissue of a patient such that the expandable isolation member inhibits fluid and electrical communication between the first electrode and the second electrode when engaged with tissue of the patient; and
wherein the one of the first electrode and the second electrode positioned distal to the distal end of the expandable isolation member comprises a pair of ring electrodes separated by an insulating member, wherein the pair of ring electrodes is configured to map the tissue of the patient, and
wherein the electrode pair is configured to be selectively energized to apply a first amount of voltage, during the electroporation therapy, and an increased second amount of voltage based on a determined level of sealing between the circumferential sealing surface and the tissue being reduced.

12. The electrode assembly of claim 11, wherein the expandable isolation member comprises an inflatable balloon.

13. The electrode assembly of claim 12, wherein the inflatable balloon is coupled to a fluid source for selectively inflating the balloon.

14. The electrode assembly of claim 13, wherein the fluid source comprises a dielectric fluid.

15. The electrode assembly of claim 13, wherein the fluid source comprises a fluid selected from the group consisting of deionized water, saline, carbon dioxide gas, nitrous oxide gas, and air.

16. The electrode assembly of claim 11, wherein the expandable isolation member comprises an outer layer constructed of electrically-insulating material.

17. The electrode assembly of claim 16, wherein the outer layer comprises polyethylene terephthalate.

18. The electrode assembly of claim 11, further comprising a distal tip electrode positioned distal to the one of the first electrode and the second electrode positioned distal to the distal end of the expandable isolation member.

19. The electrode assembly of claim 18, wherein the distal tip electrode and one of the first electrode and the second electrode are configured to be selectively energized for delivery of electroporation therapy.

\* \* \* \* \*